United States Patent [19]
Sawa et al.

[11] Patent Number: 5,865,982
[45] Date of Patent: Feb. 2, 1999

[54] PROCESS FOR PREPARING COMPOUND

[75] Inventors: Haruo Sawa; Hidetoshi Abe, both of Fukushima, Japan

[73] Assignee: Furukawa Denchi Kabushiki Kaisha, Kanagawa, Japan

[21] Appl. No.: 876,981

[22] Filed: Jun. 16, 1997

[30] Foreign Application Priority Data

Jun. 21, 1996 [JP] Japan .................................. 8-161664

[51] Int. Cl.$^6$ ...................................................... C25B 3/00
[52] U.S. Cl. .......................................... 205/413; 205/462
[58] Field of Search ..................................... 205/413, 462

[56] References Cited

U.S. PATENT DOCUMENTS 4,092,129  5/1978  Goudal ...................................... 48/210
5,665,218  9/1997  Ashizawa et al. ...................... 205/171

FOREIGN PATENT DOCUMENTS

2 322 115 A  3/1977  France .

*Primary Examiner*—Kathryn Gorgos
*Assistant Examiner*—Edna Wong
*Attorney, Agent, or Firm*—Frishauf, Holtz, Goodman, Langer & Chick, P.C.

[57] ABSTRACT

Disclosed is a novel process for preparing a compound, in which materials difficult to prepare at low temperature can be prepared even if the temperature is such a low temperature as room temperature. In this process, a solid catalyst is disposed in a vessel, a sub-reaction field f is formed on the surface of the solid catalyst, and materials for reaction are supplied to the sub-reaction field f whereby the reaction is progressed to synthesize an objective compound.

11 Claims, 6 Drawing Sheets

PROCESS FOR PREPARING COMPOUND

BACKGROUND OF THE INVENTION

1. Field of the Invention

This invention relates to a novel process for preparing a compound, especially to a process capable of preparing, at around a normal temperature, such a compound which is difficult to produce by a conventional process or which can be produced only at a high temperature.

2. Prior Art

In conventional processes for preparing an objective compound, for example, in an organic synthetic chemical field, raw materials are introduced into a reaction vessel in a simple manner, the processing conditions such as pressure, temperature, and the like are appropriately selected, and a stirring treatment is entirely performed to proceed the synthesis. Also, when the synthetic reaction is performed with the intention of synthesizing the compound under milder condition such as at a lower temperature under a lower pressure, a catalyst having fixed activities is introduced into the reaction system.

At this time, a catalyst having specific activities on the reaction system is selected and a solid catalyst is often used as the catalyst.

Generally, the catalytic activities of these catalysts are defined by the characteristics of the catalyst, for example, physical and chemical characterization factors including the adsorbing behavior to materials composed of the reaction system, surface area, pore structure, atomic arrangement of the surface, state of crystal lattice defect, and degree of acidity or basicity. This suggests that no solid catalyst having catalytic activities to every reaction system can be prepared. Specifically, a specific catalyst having specific catalytic activities corresponds to a specific reaction system.

For example, a transition metal such as Ni, Pd, Pt, or the like is used for hydrogenation of an unsaturated hydrocarbon; transition metal oxide such as $MoO_3$, $V_2O_5$ is used for selective oxidation of an organic compound; and $SiO_2$, $Al_2O_3$, zeolite, or the like is used for cracking of hydrocarbon or isomerization of a hydrocarbon as a solid catalyst.

In conventional methods for using a solid catalyst, the catalytic activities exhibiting only depending on the above physical and chemical characterization factors which the solid catalyst itself possesses is utilized. Hence there are limitations to the degree of the activities. Also, there is no guarantee that a material exhibiting high catalytic activities on a desired synthetic reaction is always available.

On the other hand, there is a case where an objective reaction does not rapidly proceed, for example, at normal temperature even if a solid catalyst is utilized in a reaction system. In this case, it is necessary to supply certain energy externally to the reaction system.

Generally, as the above energy, heat energy is conventionally used, specifically, to heat a reaction vessel externally and thereby to maintain a reaction system in a required high temperature condition. The above reaction system includes the known reaction in which stable oxides of carbon such as $CO_2$, a carbonate ion ($CO_3^{2-}$), or the like are reduced to synthesize hydrocarbon or other useful organic compound. The reaction system of this type has attracted remarkable attention as a method for absorbing $CO_2$ from an atmosphere to transform it to a useful compound by utilizing excessive energy or natural energy though it has lately been apprehended that the increase in the concentration of $CO_2$ was a cause of the rise in the temperature of the earth.

The synthetic reaction in this reaction system is known as the reaction for producing CO according to the following formula (1) and producing a higher hydrocarbon according to the following formula (2), which are described in Catalyst Lecture Vol. 9, page 84, (edited by Catalyst Society; published by Kodan Co., Ltd.):

$$CO_2 + H_2 \rightarrow CO + H_2O \qquad (1)$$

$$nCO + (2n+1)H_2 \rightarrow C_nH_{2n+2} + nH_2O \qquad (2)$$

Here, a temperature close to 1000° C. is required to progress the reaction of the formula (1) sufficiently. It is, therefore, necessary to heat a reaction vessel externally, resulting in large-scale installation.

Also, the reaction of the formula (2) is so-called "Fisher-Tropsch reaction". This reaction is progressed by method in which a catalyst is fed into a reaction vessel and CO and $H_2$ are introduced into the reaction vessel.

The reaction of the formula (2) is an exothermic reaction so that it is fundamentally unnecessary to supply energy required for reaction. However, it is necessary for the reaction system to be controlled at 150° C.—several hundreds degree ° C. under normal pressure—10 atms to accelerate the reaction velocity sufficiently even if a solid catalyst such as Co is fed.

However, even though the heat energy supplied externally to the reaction vessel is indispensable for activating the materials involved in the reaction, it is not always required for other materials. Even in this case, it is required to heat the entire of the reaction system uniformly in a conventional method for supplying heat energy.

In the conventional method for supplying heat energy, an excessively large amount of heat energy is supplied to the reaction system. There is the drawback of a large energy loss in relation to the supply of the heat energy to be required for the objective reaction system.

Also, the equipment for synthesis requires large-scaled installation and the system in which the heat energy is externally supplied indispensably causes high costs taking measures for heat resistance and anti-corrosion into consideration.

On the other hand, an electrolytic synthetic system is known as a peculiar synthetic system.

In this electrolytic synthetic system, a specific electrolyte is filled in a reaction vessel in which a pair of electrodes consisting of positive and negative poles are disposed. Voltage is induced between the electrodes so that an electrochemical reaction is formed on the surface of the electrodes and thereby to synthesize a target compound.

In this reaction system, the energy required for the reaction is supplied directly to the materials in the reaction vessel in the form of electric energy. Therefore, it is unnecessary to heat the reaction vessel externally to supply heat energy to the reaction system even if the reaction system is endothermic reaction system.

In this electrolytic synthetic system, the surface of the electrodes disposed in the electrolyte is the actual field in which the synthetic reaction proceeds. In this system, therefore, the electrodes act as a kind of solid catalyst.

Incidentally, it is thought that the reactions of the above formulae (1) and (2) can be processed by the electrolytic reaction system. In this case, because the energy to be supplied is electric energy, the reactions of the formulae (1) and (2) can be carried out at around normal temperature. In view of this, various electrodes as the solid catalyst have been investigated.

However, in almost all of cases, only the reaction of the formula (1) proceeds to terminate the objective reaction or the products to be prepared are limited to very simple organic compounds such as methane, formic acid, and the like (see Chemistry and Chemical Industry, Vol. 43, page 2016–2017, 1990).

Specifically, it is difficult to progress a C—C bonding reaction and a hydrogen abstracting reaction for forming a C=C bond from a C—C bond in the conventional electrolytic synthetic reaction system.

In addition, since the catalytic activities of the electrodes acting as the solid catalyst are also defined by its physical and chemical characterization factors, it is required for heat energy to be supplied externally to the reaction system if the catalytic activity in the reaction system is insufficient.

OBJECTS AND SUMMARY OF THE INVENTION

Accordingly, it is an object in the present invention to provide a process for preparing a compound, wherein an objective compound can be produced at normal temperature even if heat energy is not externally supplied to a reaction system when a synthetic reaction is carried out using a solid catalyst.

The present inventors directed their attentions to the following empirical facts in the course of extensive studies to attain the above object. Specifically, the conventional synthetic reaction using a solid catalyst proceeds by the mechanism in which a synthesis of a compound AB is synthesized directly by the reaction of a material A and a material B on the solid catalyst according to the following formula (3) by specific catalytic activities which are defined by the physical and chemical characterization factors:

$$A+B \rightarrow AB \tag{3}$$

Also, energy required to activate the materials A and B and thereby to cause the synthetic reaction is fundamentally defined by the catalytic activities on the surface of the solid catalyst. When the energy is insufficient, it is necessary to supply energy externally.

In view of this, the present inventors got the following idea by which the synthetic reaction of the objective compound AB can be progressed without supply of external energy: Specifically, when the compound AB is synthesized using the compounds A and B, a reaction which does not cause an obstacle to the synthesis of the compound AB and which releases a fixed energy is formed on the surface of the solid catalyst by some means to form a field of the released energy on the surface of the solid catalyst and the materials A and B are supplied in that field to promote the excitation of the materials A and B.

Based on this idea, the inventors continued extensive studies and, as a result, confirmed that various compounds could be synthesized at normal temperature even if, for example, heat energy is not externally supplied to the reaction system to complete the present invention. Accordingly, the above object can be attained in the present invention by a provision of a process for preparing a compound, comprising:

a step of forming a sub-reaction field accompanied by a release of energy on or close to the surface of a solid catalyst disposed in a reaction vessel;

a step of supplying, to the sub-reaction field, the materials concerned to a main reaction; and a step of proceeding the main reaction; to prepare the compound.

Especially, the above object can also be attained by a provision of a process for preparing a compound comprising:

a step of putting an electrolyte into a reaction vessel and disposing positive and negative electrodes in the electrolyte;

a step of inducing voltage between the positive and negative electrodes to generate an electrolytic reaction and to form a sub-reaction field accompanied by a release of energy on or close to the surface of the positive electrode and/or the surface of the negative electrode;

a step of supplying, to the sub-reaction field, the materials concerned to a main reaction; and a step of proceeding the main reaction; to prepare the compound.

DETAILED DESCRIPTION OF THE INVENTION

The present invention will now be explained in detail with reference to drawings.

Figure 1:
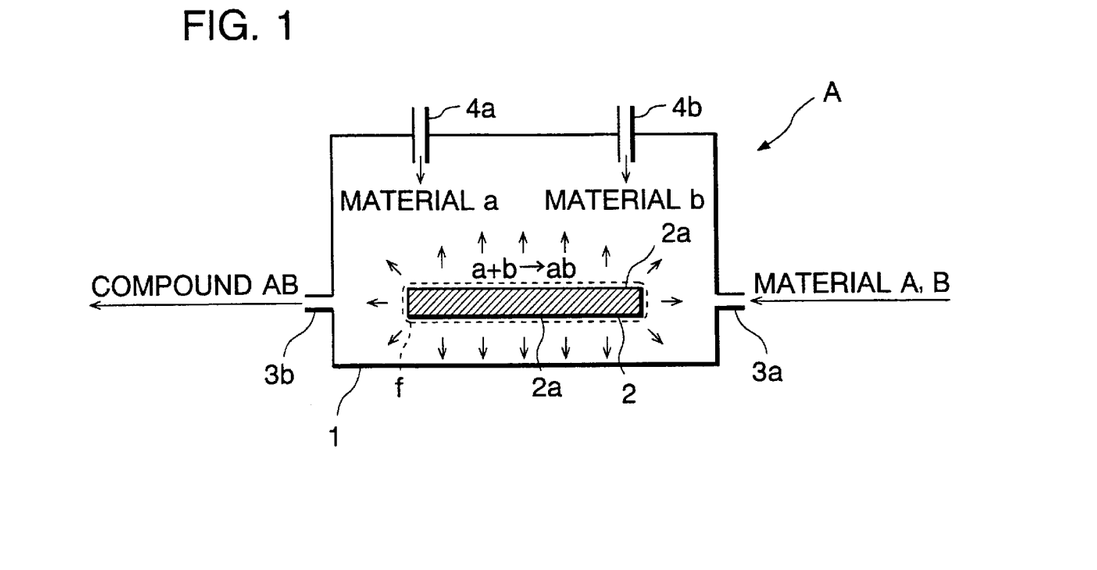
FIG. 1 is a view showing a principal structure of a system A in an embodiment according to the present invention.

FIG. 1 is a view showing a principal structure of a system A in an embodiment according to the present invention.

In FIG. 1, a solid catalyst 2 described below is disposed in a reaction vessel 1. A material introduction port 3a provided with a flow control valve (not shown) is provided at one side of the reaction vessel 1 and a compound discharge port 3b provided with a flow control valve (not shown) is provided at the other side of the reaction vessel 1. A material A and a material B, which are reactants, are introduced from the material introduction port 3a in a predetermined rate, respectively. A compound AB which is an objective compound synthesized by a reaction (described below) on the solid catalyst is discharged from the compound discharge port 3b.

Incidentally, in the present invention, the reaction which progresses between the materials A and B to produce the compound AB is called hereinafter "main reactions".

On the upper portion of the vessel 1, a material a introduction port 4a and a material b introduction port 4b both provided with flow control valves (not shown) are disposed to supply respectively a material a and a material b required for forming a sub-reaction field (described below) on or close to the surface 2a of the solid catalyst 2.

In this system A, a catalyst having the following catalytic activity is used as the solid catalyst 2 disposed in the reaction vessel 1: When the materials a and b are introduced from the material a introduction port 4a and the material b introduction port 4b respectively, these materials a and b react on the surface 2a of the solid catalyst 2 at normal temperature according to the following formula (4).

$$a+b \rightarrow ab \tag{4}$$

In this case, it is necessary that the reaction is an exothermic reaction which stationarily proceeds at normal temperature and which does not interfer with the main reaction.

Highly dense energy is released from the surface 2a of the solid catalyst 2 by the reaction of the formula (4). The released energy is diffused into the reaction vessel 1. Since the above reaction of the formula (4) stationarily proceeds, a condition higher in energy than that in the condition where the reaction of the formula (4) does not proceed is stationarily maintained on or close to the surface 2a of the solid catalyst 2. As a result, a high energy reaction field f is always formed on or close to the surface 2a of the solid catalyst 2.

In the present invention, the reaction of the formula (4) is differentiated from the reaction of the formula (3) and is called "sub-reaction". Also, the reaction field f is called "sub-reaction field".

When fixed quantities of the materials A and B are supplied from the material introduction port 3a to the sub-reaction field f while the sub-reaction field f is formed, the materials A and B are activated due to high energy maintained in the sub-reaction field f so that the main reaction of the formula (3) proceeds to produce the compound AB, which is withdrawn from the compound discharge port 3b.

Supposing a synthetic reaction of the materials A and B is directly progressed on the surface of the solid catalyst 2 without the formation of the sub-reaction field f using the materials a and b, it is necessary to supply heat energy externally to the solid catalyst 2 to activate the surface of the solid catalyst 2 to the energy level of the sub-reaction field f.

However, since a high energy field is formed on the surface of the solid catalyst 2 by the reaction of the materials a and b in the system A, the main reaction proceeds at a low temperature when the materials A and B are supplied to the sub-reaction field f, even if it is required for the main reaction to be performed at a high temperature in a conventional process.

As an example of the sub-reaction for generating the main reaction, catalytic combustion reaction is given.

For example, if $H_2$ as the material a, $O_2$ as the material b, and Pt as the solid catalyst 2 are selected, the reaction shown by the following formula (5) can be stationarily progressed even at normal temperature:

$$H_2 + (\frac{1}{2})O_2 \rightarrow H_2O \quad (5)$$

In the case of the reaction shown by the formula (5), high dense energy is released from the surface of the Pt catalyst in the forms of light, produced exited substances including various radicals, ions, and the like, molecular motion, and the like to form the sub-reaction field f.

In this sub-reaction field f, the materials A and B supplied into the reaction system directly receives the high dense energy in the sub-reaction field f by means of the transfer of light, transfer of energy through contact with the excited substances, and the like, whereby the materials A and B are excited so that the main reaction proceeds in the sub-reaction filed f to produce the compound AB.

Also, as other sub-reaction, reactions for oxidizing a variety of metals or organic compounds by oxygen, for hydrogenating metals by hydrogen, and for reducing metal oxides by hydrogen, and the like are exemplified.

The sub-reaction used in the present invention must be a reaction which releases energy, specifically exothermic reaction, which progresses at a comparatively low temperature on the surface of the solid catalyst, and which does not cause an obstacle to the main reaction.

In the case of an oxidative reaction using oxygen as a sub-reaction, inexpensive air may be used instead of oxygen. Also, the catalyst may contain metals such as Pt, Pd, Ni, Cu, or the like to proceed the sub-reaction smoothly.

Figure 2:
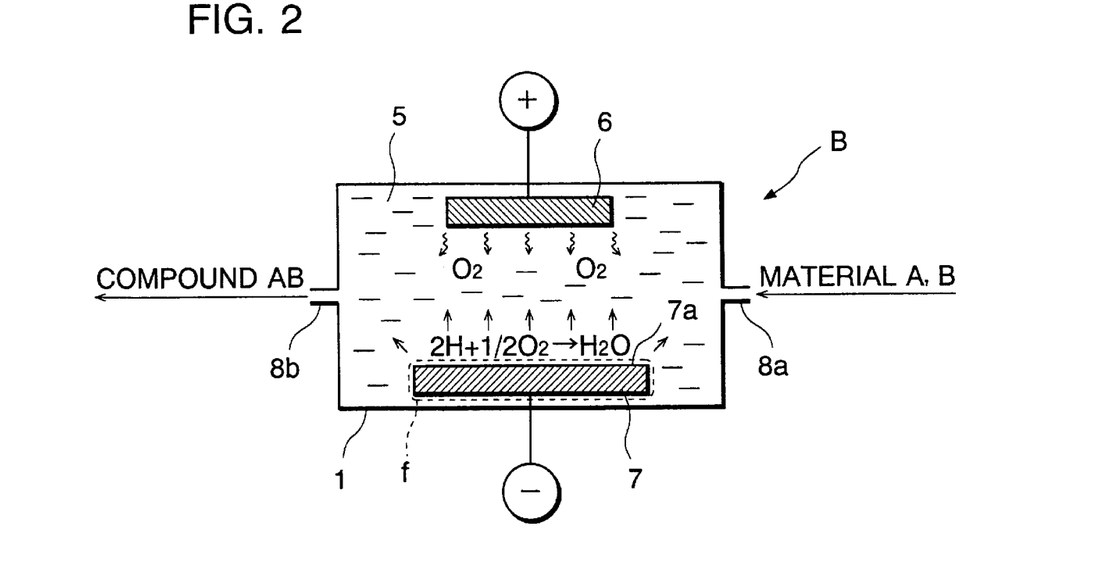
FIG. 2 is a view showing a principal structure of a system B in another embodiment according to the present invention.

FIG. 2 is a view showing a principal structure of a system B in another embodiment according to the present invention.

This system B has a structure in which an electrolyte 5 described below is contained in a reaction vessel 1, a pair of electrodes consisting of a positive electrode 6 connected to a plus power source and a negative electrode 7 connected to a minus power source are disposed in the electrolyte 5, a introduction port 8a for introducing materials A and B is provided at one side of the reaction vessel 1, and a discharge port 8b for discharging a compound AB is provided at the other side of the reaction vessel 1.

In this system B, the above positive electrode 6 and/or negative electrode 7 act as a solid catalyst so-called in the present invention. The entire structure of the system B is similar to that of the system in which a gas component generating from one electrode is absorbed by the other electrode to restrain the rise of the internal pressure in a secondary battery when the secondary battery is excessively charged.

In this system B. voltage is induced between the electrodes 6 and 7 to proceed the electrolytic reaction of the electrolyte 5.

At this time, the structural conditions are designed so that the above negative electrode 7 includes a metal such as Zn, Cd, Fe or the like or an oxide (hydroxide) of these metals, which is conventionally used as an active material for the negative electrode of an alkaline secondary battery, metal such as Co, Cu, Pb, Ni, Au, Ag, or the like or an oxide (hydroxide) of these metals, which is not an active material, and/or a hydrogen storage alloy or the like, and $O_2$ is primarily generated from the positive electrode 6. With the above structure, $O_2$ generated from the positive electrode 6 is diffused to the surface 7a of the negative electrode 7 to react with hydrogen or metal whereby $O_2$ is absorbed. As a result, a high energy sub-reaction field f is formed on or close to the surface 7a of the negative electrode 7.

Also, if the structural conditions are designed so that a metal such as Ni, Ag, Mn, Co, Cu or the like or an oxide (hydroxide) of these metals is contained in the positive electrode 6 and $H_2$ is primarily generated from the negative electrode 7, a high energy sub-reaction field f is formed on or close to the surface 6a of the positive electrode 6 in the same manner as above.

Then, the synthesis of the compound AB is progressed by supplying the compounds A and B in the sub-reaction field f.

As a supply embodiment, the materials A and B may be introduced directly into the reaction vessel 1 in a fixed amount while the sub-reaction field f is stationarily formed. Also, if the materials A and B are soluble in the electrolyte 5, these materials A and B are dissolved in the electrolyte in advance to form the sub-reaction field f as it stands. The latter is suitable because the objective main reaction proceeds smoothly and efficiently.

When the sub-reaction field f is formed using the above-described positive electrode 6 and the negative electrode 7, an alkaline electrolyte such as an aqueous KOH solution, aqueous NaOH solution, aqueous LiOH solution, or mixture of these are used since the component contained in the positive or negative electrode is an active material for alkaline secondary battery. There is a case that it is suitable to use an acidic electrolyte depending on the kind of the reaction system. In such a case, an active material used for a lead battery is contained in the positive or negative electrode and an aqueous sulfuric acid solution is used as the electrolyte, whereby a similar sub-reaction field can be formed.

In the system B, a porous separator may be arranged between the positive electrode 6 and the negative electrode 7 to avoid development of a short circuit across the both electrodes in the same manner as in the structure adopted for a secondary battery.

In addition, it is desirable that the vessel 1 be not filled with a liquid but be occupied with a gas in a certain degree so that a material required for forming the sub-reaction field f, that is, a gas component generated from the positive electrode 6 or the negative electrode 7 can rapidly diffuse and move between the both electrodes and the sub-reaction can be progressed at a large rate.

EXAMPLE 1

The system B shown in FIG. 3 was fabricated as follows:
1) Preparation of Positive electrode and Negative electrode 4 g of $Ni(OH)_2$ powder with an average diameter of approximately 10 $\mu$m was filled into a nickel sponge with a porosity of 96%, which was then rolled to produce a positive electrode sheet of 70 mm length, 40 mm wide, 0.57 mm thickness.

8 g of a hydrogen storage alloy having the composition of $MmNi_{3.2}Co_{1.0}Al_{0.2}Mn_{0.4}$ (Mm is a misch metal containing 49% by weight of Ce and 25% by weight of La) together with a PTFE binding agent was applied to a panting metal sheet which comprises Ni plated stainless steel(numerical aperture: 40%, opening diameter: 1.5 mm, thickness: 70 $\mu$m), which was then rolled to prepare a negative electrode sheet of 100 mm length, 40 mm wide, 0.35 mm thickness.
2) Fabrication of system B Next, as a separator 9, a polypropylene nonwoven fabric with a thickness of 0.15 mm was sandwiched between the positive electrode 6 and negative electrode 7 and these were entirely wound up to a diameter of 13 mm so that the negative electrode 7 was located externally, which was then inserted into a cylindrical can 1a with a bottom made f Ni plated stainless steel with an internal diameter of 140 mm and a height of 500 mm. In this case, the negative electrode 7 was inserted so that it contacted the internal wall of the cylindrical can 1a.

Then, 1.98 mdm$^3$ of the alkaline electrolyte 5 consisting of 5% by weight of $K_2CO_3$, 30% by weight of KOH, and 1.0% by weight of LiOH was charged into the cylindrical can 1a with a bottom. The upper opening of the cylindrical can was sealed with a lid 1b through an insulating material 1c. Here, the positive electrode 6 was electrically connected to the lid 1b.

A pressure sensor 11 and a closing valve 12 was installed with the lid 1b through thin pipe 10 having a diameter of 1 mm.

In this system B, the negative electrode 7 acted as a solid catalyst and the materials A and B were $CO_2(CO_3^{2-})$ dissolved in the electrolyte 5.
3) Result of synthetic reaction In the system B fabricated in this manner, a closing valve 12 was closed, the lid 1b was connected to a plus power source, the cylindrical can 1a with a bottom was connected to a minus power source, and 550 mA current was induced for 5 hours.

The electrolytic reaction of the electrolyte 5 was proceeded by this energizing, whereby $O_2$ was primarily generated from the positive 6 and hydrogen was absorbed into the hydrogen storage alloy of the negative electrode 7. $O_2$ diffused and transferred to the negative electrode 7 and a sub-reaction was progressed on the electrode 7 whereby $O_2$ was combined with hydrogen in the alloy.

The pressure in the reaction vessel by a pressure sensor 11 which was measured during the energizing was maintained almost at 3 atms. Also, the temperature of the external wall of the cylindrical can 1a with a bottom was measured. The temperature was maintained almost at 35° C.

Namely, the above-described sub-reaction stationarily proceeded during the energizing. This sub-reaction was an exothermic reaction.

During the current induction, the closing valve 12 was opened intermittently to sample the gas in the vessel 1 from a thin pipe 10. The gas components were analyzed by means of gas chromatography. The results are shown in FIG. 4.

Figure 4:
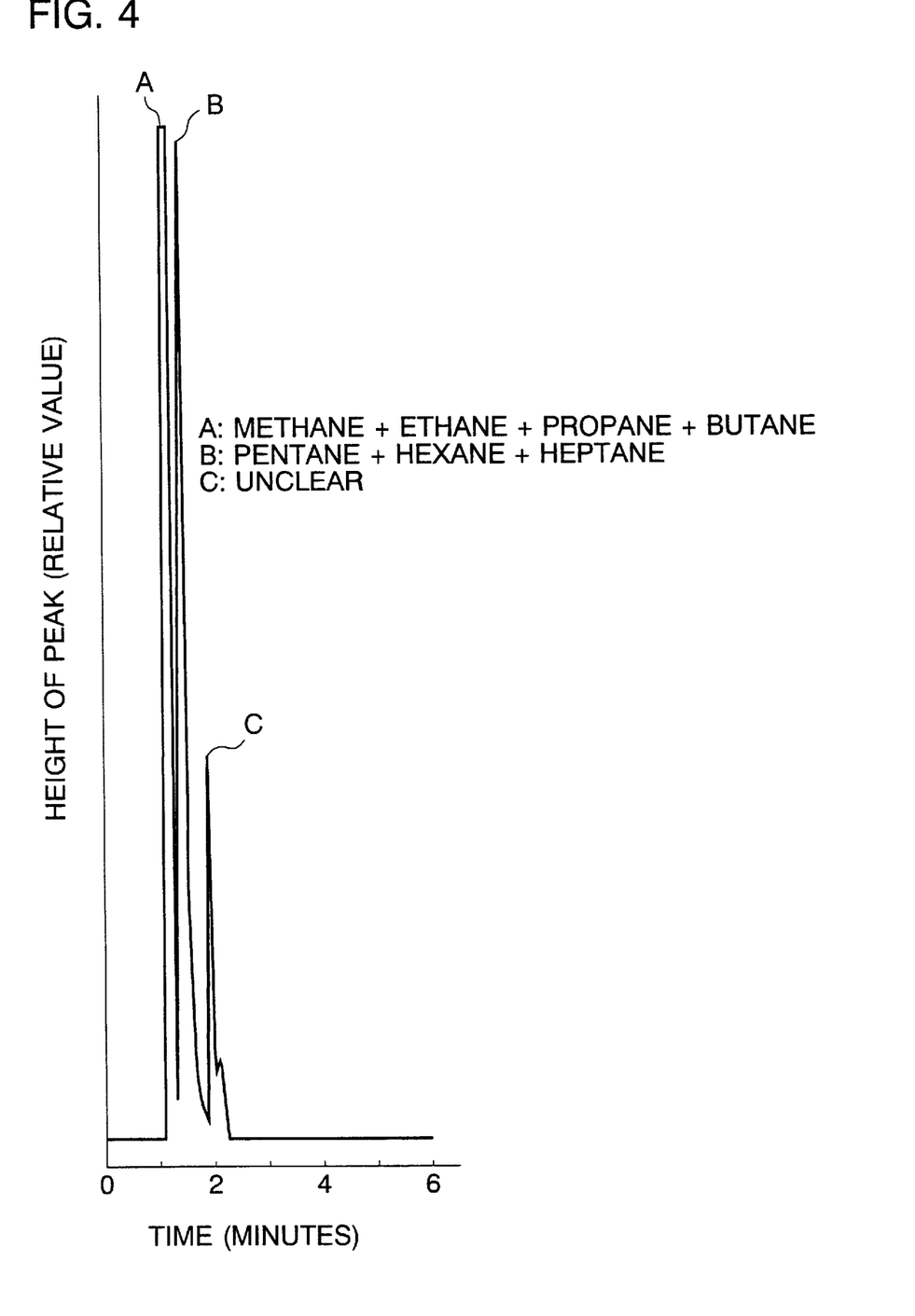
FIG. 4 is a graph showing a result of chromatography in EXAMPLE 1.

In FIG. 4, the peak A shows existence of methane, ethane, propane, and butane and the peak B shows existence of pentane, hexane, and heptane. Incidentally, the peak C is not clarified.

Figure 3:
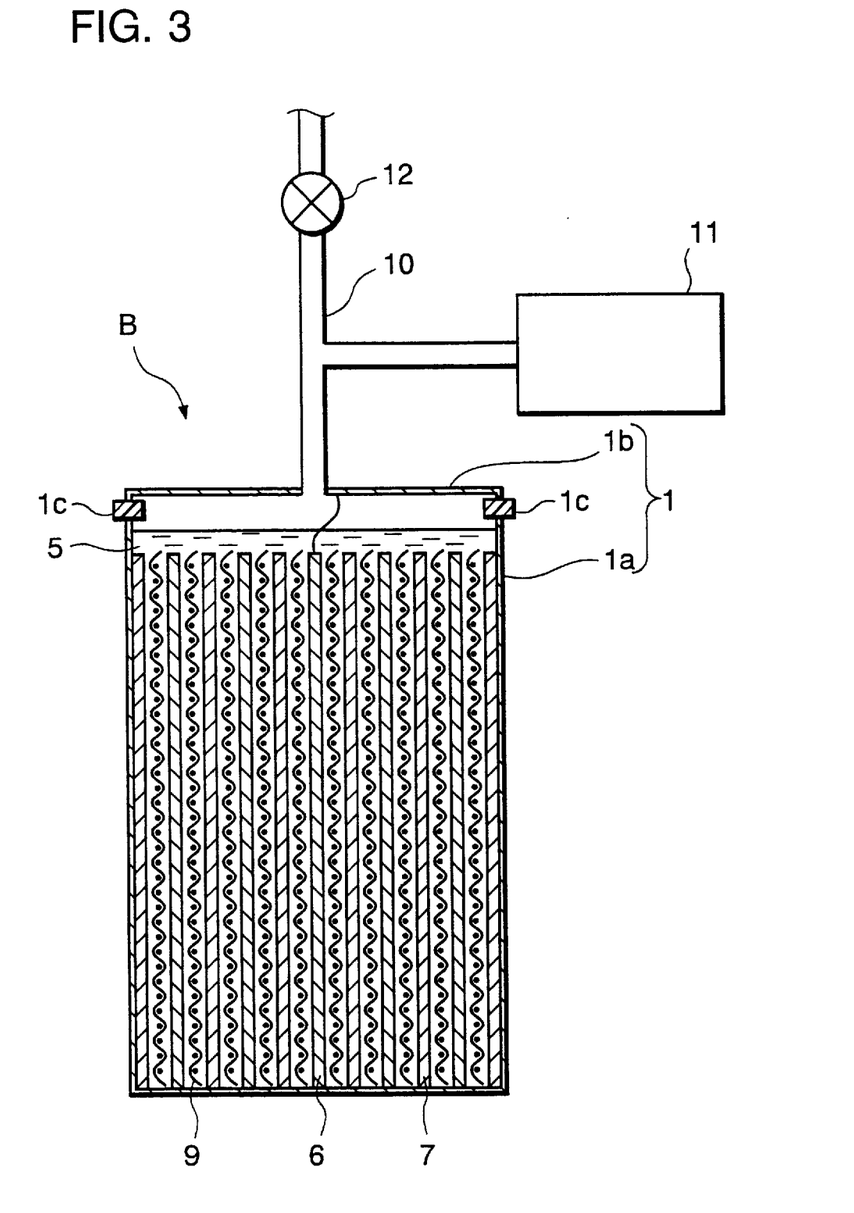
FIG. 3 is a view schematically showing the system B of the present invention arranged according to the EXAMPLE 1.

As is clear from FIG. 4, when the system B shown in FIG. 3 is operated, methane, ethane, propane, butane, pentane, hexane and heptane can be produced at 35° C., specifically close to room temperature.

EXAMPLE 2

The system B was operated in the same manner as in EXAMPLE 1 except that an alkaline electrolyte consisting of 30% by weight of KOH and 1.0% by weight of LiOH was used as the electrolyte and 1.0 mdm$^3$ of methane gas was introduced through the thin pipe 10 to seal up methane gas into the reaction system before energizing.

In this case, the pressure in the reaction vessel 1 during the energizing was maintained almost at 3 atms. Also, the temperature of the external wall of the cylindrical can 1a was maintained almost at 35° C.

Figure 5:
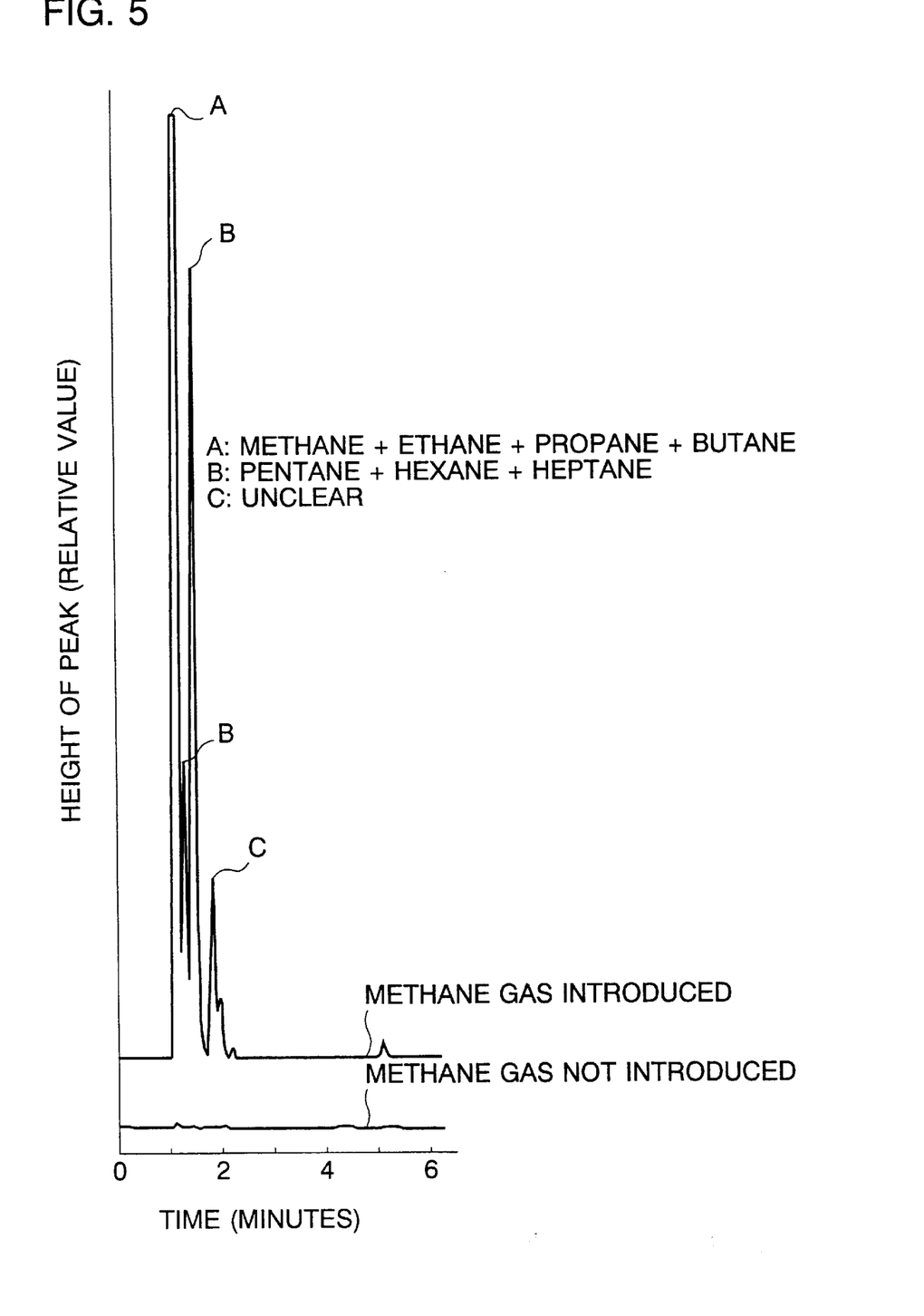
FIG. 5 is a graph showing a result of chromatography in EXAMPLE 2.

Gas components in the reaction vessel 1 was analyzed by means of gas chromatography in the same manner as in EXAMPLE 1. The results are shown in FIG. 5. In FIG. 5, the results of gas chromatography in the case where methane was not sealed up into the reaction system also was shown for comparison.

As is clear from FIG. 5, with the system B of the present invention, ethane, propane, butane, pentane, hexane, and heptane were synthesized using methane gas as a starting material at 35° C., specifically close to room temperature.

Comparative Example

Figure 6:
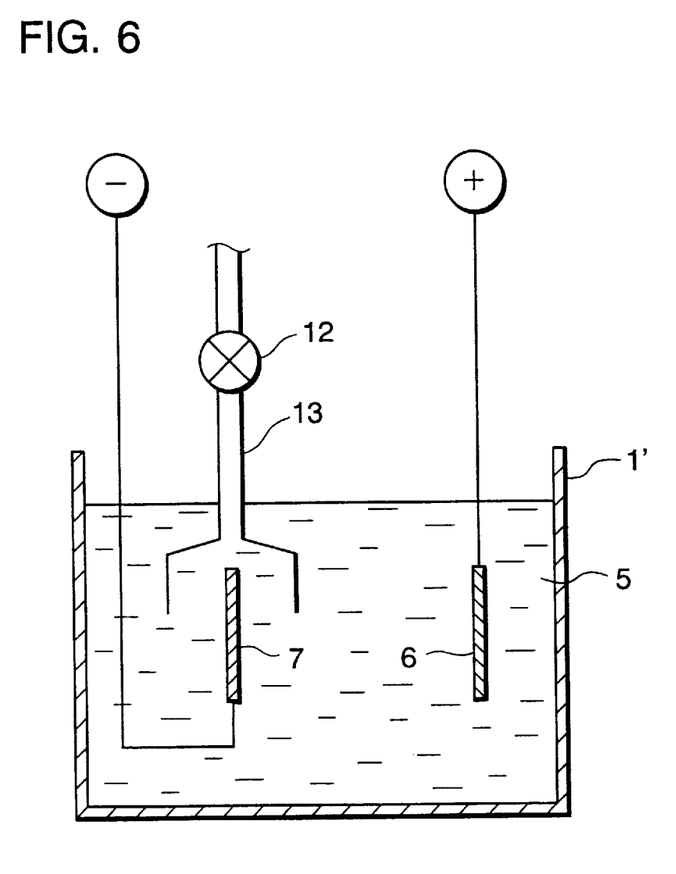
FIG. 6 is a view showing a conventional system for performing electrolytic synthesis.

A conventional electrolytic synthesis was tried for comparison. Specifically, as shown in FIG. 6, an electrolyte 5 used in EXAMPLE 1 was filled in an electrolytic vessel 1'. A positive electrode 6 and a negative electrode 7 used in EXAMPLE 1 were disposed oppositely.

A cover 13 provided with a closing valve 12 is disposed so that it entirely covers the negative electrode 7. In this condition, the both electrodes were energized in the same condition as in EXAMPLE 1.

Figure 7:
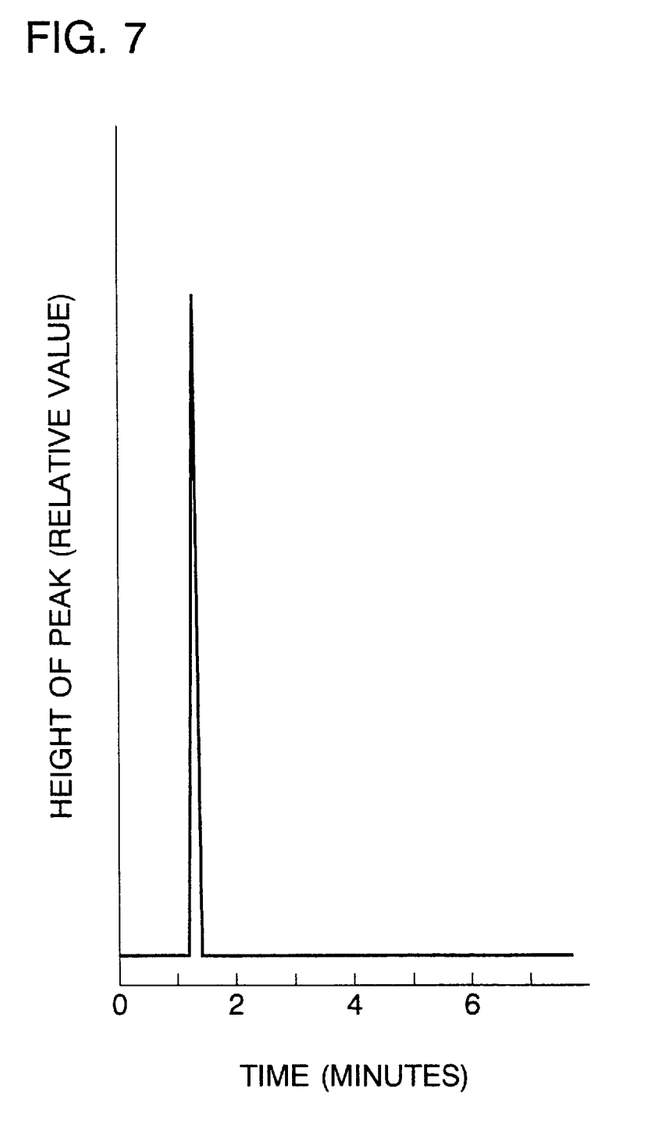
FIG. 7 is a graph showing a result of chromatography in the system illustrated in FIG. 6.

The closing valve 12 was opened, generated gas was sampled from the cover 13, and it was analyzed by means of gas chromatography. The results are shown in FIG. 7.

One peak was observed. This peak shows the existence of methane.

As is clear from the above explanations, in the present invention, even if the reaction system is not higher in the temperature by externally heating the reaction system, an objective compound can be obtained at around normal temperature.

This is effects based on the provision in which a sub-reaction field releasing energy is formed on the surface of a solid catalyst and a main reaction of an objective compound proceeds in the sub-reaction field.

What is claimed is:

1. A process for preparing a compound, comprising:

putting an electrolyte into a reaction vessel and disposing positive and negative electrodes in said electrolyte;

inducing voltage between said positive and negative electrodes to generate an electrolytic reaction to generate oxygen at the positive electrode and hydrogen at the negative electrode, to cause a sub-reaction, said sub-reaction being a reaction in which oxygen generated from the positive electrode reacts with hydrogen on the surface of the negative electrode or with a metal of the negative electrode, or a reaction in which hydrogen generated from the negative electrode reduces a metal oxide of the positive electrode; or a combination of these reactions;

supplying, to the field of said sub-reaction, reactants to be reacted in a main reaction to form target compounds; and allowing said main reaction to proceed to form the target compounds.

2. A process for preparing a compound according to claim 1, wherein the negative electrode includes at least one selected from the group consisting of Zn, Fe, Cd, Co, Cu, Pb, Ni, Pt, Pd, Au, Ag; oxides and hydroxides thereof; and a hydrogen storage alloy, its hydride, and mixtures thereof.

3. A process for preparing a compound according to claim 2, wherein the positive electrode includes at least one selected from the group consisting of oxides and hydroxides of a metal selected from the group consisting of Ni, Mn, Co, Cu and Ag;

a metal selected from the group consisting of Ni, Pt, Pd, and Cu; and mixtures thereof.

4. A process for preparing a compound according to claim 3, wherein the electrolyte is at least one of an electrolyte selected from the group consisting of an aqueous potassium hydroxide solution, aqueous sodium hydroxide solution, aqueous lithium hydroxide solution; and aqueous sulfuric acid;

the reactants participating in the main reaction include any one of $CO_2$, $CO_3^{2-}$, and $CH_4$; and the target compounds include a hydrocarbon.

5. A process for preparing a compound according to claim 4, wherein a porous separator is disposed between the positive electrode and the negative electrode.

6. A process for preparing a compound according to claim 1, wherein the positive electrode includes at least one selected from the group consisting of oxides and hydroxides of a metal selected from the group consisting of Ni, Mn, Co, Cu and Ag;

metal selected from the group consisting of Ni, Pt, Pd, and Cu; and mixtures thereof.

7. A process for preparing a compound according to claim 1, wherein the electrolyte is at least one of an electrolyte selected from the group consisting of an aqueous potassium hydroxide solution, aqueous sodium hydroxide solution, aqueous lithium hydroxide solution and an aqueous sulfuric acid.

8. A process for preparing a compound according to claim 1, wherein a porous separator is disposed between the positive electrode and the negative electrode.

9. A process for preparing a compound according to claim 1, wherein the reactants participating in the main reaction and the target compounds are all carbon compounds.

10. A process for preparing a compound according to claim 1, wherein the reactants participating in the main reaction include any one of $CO_2$, $CO_3^{2-}$, and $CH_4$; and the target compounds include a hydrocarbon.

11. A process for preparing a compound comprising:

placing an electrolyte containing potassium hydroxide in a reaction vessel;

disposing a positive electrode including nickel hydroxide and a negative electrode including a hydrogen storage alloy in said electrolyte;

inducing a voltage between the positive electrode and negative electrode to generate oxygen; and reacting the generated oxygen and hydrogen stored in the hydrogen storage alloy of the negative electrode on or close to the surface of the negative electrode while reactants including any one of $CO_2$, $CO_3^{2-}$, and $CH_4$ are supplied close to the surface of the negative electrode; to prepare compounds including a hydrocarbon.

* * * * *